United States Patent
Nihei et al.

(10) Patent No.: US 8,963,142 B2
(45) Date of Patent: Feb. 24, 2015

(54) PHOTOELECTRIC TRANSDUCER AND SOLID-STATE IMAGING APPARATUS

(75) Inventors: Ayumi Nihei, Tokyo (JP); Masaki Murata, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/808,014

(22) PCT Filed: Apr. 25, 2011

(86) PCT No.: PCT/JP2011/060566
§ 371 (c)(1),
(2), (4) Date: Feb. 12, 2013

(87) PCT Pub. No.: WO2012/005048
PCT Pub. Date: Jan. 12, 2012

(65) Prior Publication Data
US 2013/0134409 A1     May 30, 2013

(30) Foreign Application Priority Data
Jul. 9, 2010   (JP) .................................. 2010-156642

(51) Int. Cl.
H01L 51/00   (2006.01)
C07D 277/20  (2006.01)
C07D 277/50  (2006.01)
C09B 29/033  (2006.01)
(Continued)

(52) U.S. Cl.
CPC .......... *H01L 51/0069* (2013.01); *C07D 277/20* (2013.01); *C07D 277/50* (2013.01); *C09B 29/0085* (2013.01); *C09B 29/12* (2013.01); *H01L 51/0059* (2013.01); *C09K 11/06* (2013.01); *H05B 33/02* (2013.01); *H01L 27/307* (2013.01); *H01L 51/42* (2013.01); *C09K 2211/1037* (2013.01)

USPC ............... 257/40; 257/E51.006; 257/E51.024

(58) Field of Classification Search
USPC ........................................................... 257/40
See application file for complete search history.

(56) References Cited

U.S. PATENT DOCUMENTS

2006/0278869 A1   12/2006   Hioki et al.
2009/0289248 A1   11/2009   Kobayashi et al.
(Continued)

FOREIGN PATENT DOCUMENTS

JP   2006-339424 A   12/2006
JP   2007-088033 A   4/2007
(Continued)

OTHER PUBLICATIONS

Higashino et al. Photovoltaic properties of azo compounds containing the thiazole group. J. Photochem. Photobiol. A: Chem. 1994;79:81-8.
(Continued)

*Primary Examiner* — Mamadou Diallo
(74) *Attorney, Agent, or Firm* — Wolf, Greenfield & Sacks, P.C.

(57) ABSTRACT

Provided is a photoelectric transducer having a photoelectric conversion material layer including an organic material with higher sensitivity and response than conventional one.
The photoelectric transducer includes (a-1) first and second electrodes 21 and 22 separated from each other and (a-2) a photoelectric conversion material layer 30 provided between the first and second electrodes 21 and 22, wherein the photoelectric conversion material layer 30 includes an azo moiety-containing thiazole compound represented by the structural formula (1).

19 Claims, 4 Drawing Sheets

(51) Int. Cl.
*C09B 29/12* (2006.01)
*C09K 11/06* (2006.01)
*H05B 33/02* (2006.01)
*H01L 27/30* (2006.01)
*H01L 51/42* (2006.01)

(56) References Cited

U.S. PATENT DOCUMENTS

2010/0013381 A1   1/2010  Stoessel et al.
2010/0032548 A1*  2/2010  Murata .................. 250/206
2013/0099225 A1   4/2013  Nihei et al.

FOREIGN PATENT DOCUMENTS

| JP | 2007-123707 A | 5/2007 |
| JP | 2007-311647 A | 11/2007 |
| JP | 2009-029746 A | 2/2009 |
| JP | 2009-544743 A | 12/2009 |
| JP | 2010-006794 A | 1/2010 |

OTHER PUBLICATIONS

Possamai et al., Synthesis, photophysics and photoresponse of fullerene-based azoaromatic dyads. Chem. Eur. J. 2005;11:5765-76.

Higashino et al., Yuki senryo azo kagobutsu no hikari dendo oyobi hikari kidenryoku ni okeru chikanki koka. Senryo to Yakuhin. 1996;41(6):135-49.

Kobayashi et al., Stable peri-xanthenoxanthene thin-film transistors with efficient carrier injection. Chem. Mater. 2009;21(3):552-6.

Kobayashi et al., kayosei peri-xanthenoxanthene yudotai o mochiita usumaku transistor. Dai 56 Kai Extended Abst. JP. Soci. Appl. Phys. Rel. Soc. Mar. 30, 2009;3;1390.

* cited by examiner (A)

(B)

PHOTOELECTRIC TRANSDUCER AND SOLID-STATE IMAGING APPARATUS

RELATED APPLICATIONS

This application is a U.S. National Stage application under 35 U.S.C. §371 based on International Application No. PCT/JP2011/060566, filed Apr. 25, 2011, which claims priority to Japanese Patent Application No. 2010-156642, filed Jul. 9, 2010, each of which is hereby incorporated by reference in its entirety for all purposes.

TECHNICAL FIELD

The present invention relates to a photoelectric transducer and a solid-state imaging apparatus having the photoelectric transducer.

BACKGROUND ART

Photoelectric transducers (organic photodiodes) produced using an organic material can photoelectrically convert light of only a specific color (specific wavelength range). When photoelectric transducers with such a feature are used in a solid-state imaging apparatus, a structure with layered subpixels can be obtained, which would otherwise be impossible in a traditional solid-state imaging apparatus having two-dimensionally arranged subpixels each including a combination of an on-chip color filter (OCCF) and a photoelectric transducer. Thus, since such a structure enables incident light to be received with high efficiency, it can be expected that a solid-state imaging apparatus with higher sensitivity will be provided. Such a structure is also advantageous in that no false color is generated, because it does not need mosaic processing.

On the other hand, organic photoelectric transducers for use in solid-state imaging apparatuses have the same or similar structure as various organic thin film solar cells (see for example Japanese Patent Application Laid-Open Nos. 2006-339424, 2007-123707, 2007-311647, and 2007-088033) and are aimed at increasing photoelectric conversion efficiency.

CITATION LIST

Patent Documents

Patent Document 1: Japanese Patent Application Laid-Open No. 2006-339424
Patent Document 2: Japanese Patent Application Laid-Open No. 2007-123707
Patent Document 3: Japanese Patent Application Laid-Open No. 2007-311647
Patent Document 4: Japanese Patent Application Laid-Open No. 2007-088033

SUMMARY OF THE INVENTION

Problems to be Solved by the Invention

In general, however, organic materials have high resistance and a very low level of mobility and carrier density as compared to silicon semiconductor materials. Thus, there have been yet no organic photoelectric transducers having characteristics such as sensitivity and response comparable to those of conventional photoelectric transducers produced using inorganic materials typified by silicon semiconductor materials.

It is thus an object of the present invention to provide a photoelectric transducer having a photoelectric conversion material layer including an organic material with higher sensitivity and response than conventional one, and to provide a solid-state imaging apparatus including such a photoelectric transducer.

Solutions to Problems

A photoelectric transducer according to a first embodiment of the present invention to achieve the object includes (a-1) first and second electrodes separated from each other, and (a-2) a photoelectric conversion material layer provided between the first and second electrodes, wherein the photoelectric conversion material layer includes an azo moiety-containing thiazole compound represented by the following structural formula (1):

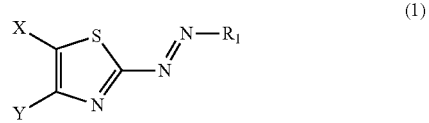

(1)

where X and Y each represent a hydrogen atom or a substituent other than a hydrogen atom, and $R_1$ represents an alkyl group, an alkenyl group, an alkynyl group, or an aryl group.

A photoelectric transducer according to a second embodiment of the present invention to achieve the object includes (a-1) first and second electrodes separated from each other, and (a-2) a photoelectric conversion material layer provided between the first and second electrodes, wherein the photoelectric conversion material layer includes an azo moiety-containing thiazole compound represented by the following structural formula (2):

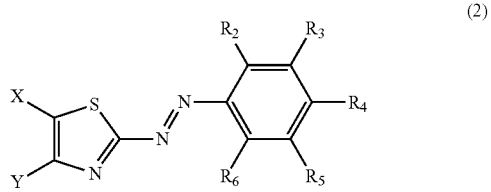

(2)

where X and Y each represent a hydrogen atom or a substituent other than a hydrogen atom, and at least one of $R_2$ to $R_6$ represents a substituent other than a hydrogen atom.

A solid-state imaging apparatus according to the first embodiment of the present invention to achieve the object includes a photoelectric transducer including (a-1) first and second electrodes separated from each other, and (a-2) a photoelectric conversion material layer provided between the first and second electrodes, wherein the photoelectric conversion material layer includes the azo moiety-containing thiazole compound represented by the structural formula (1).

A solid-state imaging apparatus according to the second embodiment of the present invention to achieve the object includes a photoelectric transducer including (a-1) first and second electrodes separated from each other, and (a-2) a photoelectric conversion material layer provided between the first and second electrodes, wherein the photoelectric conversion material layer includes the azo moiety-containing thiazole compound represented by the structural formula (2).

Effects of the Invention

The azo moiety-containing thiazole compound represented by the structural formula (1) or (2), which forms the photoelectric conversion material layer, has an absorption coefficient ($3\times10^4$ $dm^3$ $mol^{-1}cm^{-1}$ or more, typically from $4.5\times10^4$ $dm^3 mol^{-1}cm^{-1}$ to $5.0\times10^4$ $dm^3$ $mol^{-1}cm^{-1}$) higher than the absorption coefficient (about $1.4\times10^4$ $dm^3$ $mol^{-1}cm^{-1}$) of a common organic dye (e.g., quinacridone), and can achieve an increase in photocurrent. Various substituents can be introduced to positions X, Y, $R_1$, and $R_2$ to $R_6$ so that the absorption wavelength can be selected as desired in the range of 400 nm to 800 nm. In addition, the compound has a deep HOMO level and a high energy barrier against an electrode, which makes it possible to suppress dark current (charge injection) even when a high bias is applied. In addition, since the compound has a high absorption coefficient, the photoelectric conversion material layer can be made thinner. This makes it possible to provide a photoelectric transducer and a solid-state imaging apparatus each having high sensitivity and high response speed. The organic semiconductor material used to form the photoelectric conversion material layer also has high flexibility in designing the molecule, and the molecule is easy to design. The use of the compound also makes it possible to improve process adaptability. Specifically, the photoelectric conversion material layer can be formed not only by PVD but also by what is called wet process, such as coating or printing process. Thus, this makes it possible to easily produce a high-performance photoelectric transducer. In addition, the substituents can be easily introduced, and the absorption wavelength can be selected by selecting appropriate substituents, so that a photoelectric conversion material layer capable of absorbing light with a specific wavelength can be provided. Thus, when the photoelectric transducer of the present invention is used to form a solid-state imaging apparatus, no on-chip color filter is necessary, and a multi-layered structure of photoelectric transducers can be provided. In addition, photoelectric transducers and solid-state imaging apparatuses can be provided using a very simple structure without using p-n junctions, p-i-n junctions, bulk heterostructures, multilayer formation, or other traditional techniques required frequently.

MODE FOR CARRYING OUT THE INVENTION

Figure 1:
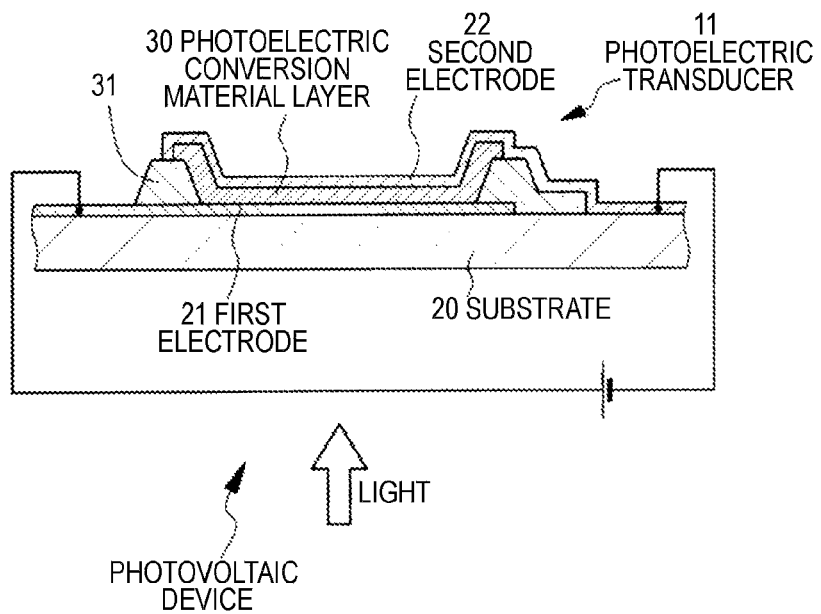
FIG. 1 is a schematic cross-sectional view of a photoelectric transducer of Example 1.

Hereinafter, the present invention is described based on examples with reference to the drawings. The examples are not intended to limit the present invention, and various values and materials shown in the examples are only illustrative. Descriptions are given in the following order.

1. Description of the general features of the photoelectric transducers and the solid-state imaging apparatuses according to the first and second embodiments of the present invention 2. Example 1 (the photoelectric transducers and the solid-state imaging apparatuses according to the first and second embodiments of the present invention) and other features [Description of the general features of the photoelectric transducers and the solid-state imaging apparatuses according to the first and second embodiments of the present invention]

In the photoelectric transducer according to the second embodiment of the present invention or the photoelectric transducer in the solid-state imaging apparatus according to the second embodiment of the present invention (hereinafter, these are also generically referred to as "the photoelectric transducer etc. according to the second embodiment of the present invention"), at least one of $R_2$ to $R_6$ is an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, and a silyl group. In the photoelectric transducer etc. according to the second embodiment of the present invention having this feature or the photoelectric transducer according to the first embodiment of the present invention or the photoelectric transducer in the solid-state imaging apparatus according to the first embodiment of the present invention (hereinafter, these are also generically referred to as "the photoelectric transducer etc. according to the first embodiment of the present invention"), X and Y may each represent a substituent other than a hydrogen atom. In this case, the substituent may be selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, and a silyl group.

The photoelectric transducer according to the first or second embodiment of the present invention having the preferred feature or the photoelectric transducer in the solid-state imaging apparatus according to the first or second embodiment of the present invention (hereinafter, these are also generically referred to as "the photoelectric transducer etc. of the invention") may include a first electrode formed of a transparent conductive material on a transparent substrate, a photoelectric conversion material layer formed on the first electrode, and a second electrode formed on the photoelectric conversion sion material layer. Alternatively, the same may include a first electrode formed on a substrate, a photoelectric conversion material layer formed on the first electrode, and a second electrode formed of a transparent conductive material on the photoelectric conversion material layer. In this structure, the first and second electrodes are separated from each other. In the separated state, the second electrode may be provided above the first electrode.

As stated above, the photoelectric transducer etc. of the invention preferably has a light-incident-side electrode made of a transparent conductive material. Such an electrode is also referred to as a "transparent electrode." Examples of the transparent conductive material used to form the transparent electrode include indium-tin oxide (ITO, including Sn-doped $In_2O_3$, crystalline ITO, and amorphous ITO), IFO (F-doped $In_2O_3$), tin oxide ($SnO_2$), ATO (Sb-doped $SnO_2$), FTO (F-doped $SnO_2$), zinc oxide (including Al-doped ZnO, B-doped ZnO, and Ga-doped ZnO), indium oxide-zinc oxide (IZO), titanium oxide ($TiO_2$), spinel type oxides, and oxides having a $YbFe_2O_4$ structure. The transparent electrode made of any of these materials generally has a relatively high work function and functions as an anode electrode. Examples of methods for forming the transparent electrode, which depend on the material used to form the transparent electrode, include physical vapor deposition (PVD) techniques such as vacuum deposition, reactive vacuum deposition, various sputtering techniques, electron beam evaporation, and ion plating, pyrosol processes, organometallic compound pyrolysis methods, spraying methods, dipping methods, various chemical vapor deposition (CVD) techniques including MOCVD techniques, electroless plating, and electroplating. In some cases, the other electrode may also be made of a transparent conductive material.

When the transparency is unnecessary and when the first or second electrode is formed to function as an anode electrode (anode), namely, to function as a hole extraction electrode, the first or second electrode is preferably made of a conductive material having a relatively high work function (e.g., $\phi$=4.5 eV to 5.5 eV). Examples of such a conductive material include gold (Au), silver (Ag), chromium (Cr), nickel (Ni), palladium (Pd), platinum (Pt), iron (Fe), iridium (Ir), germanium (Ge), osmium (Os), rhenium (Re), and tellurium (Te). On the other hand, when the first or second electrode is formed to function as a cathode electrode (cathode), namely, to function as an electron extraction electrode, the first or second electrode is preferably made of a conductive material having a relatively low work function (e.g., $\phi$=3.5 eV to 4.5 eV). Examples of such a conductive material include alkali metals (e.g., Li, Na, and K) and fluorides or oxides thereof, alkaline earth metals (e.g., Mg and Ca) and fluorides or oxides thereof, aluminum (Al), zinc (Zn), tin (Sn), thallium (Tl), sodium-potassium alloys, aluminum-lithium alloys, magnesium-silver alloys, indium, rare earth metals such as ytterbium, or alloys thereof. Other examples of the material used to form the first or second electrode include metals such as platinum (Pt), gold (Au), palladium (Pd), chromium (Cr), nickel (Ni), aluminum (Al), silver (Ag), tantalum (Ta), tungsten (W), copper (Cu), titanium (Ti), indium (In), tin (Sn), iron (Fe), cobalt (Co), and molybdenum (Mo), or alloys containing any of these metallic elements, conductive particles made of any of these metals, conductive particles of alloys containing any of these metals, and conductive materials such as impurity-doped polysilicon, carbon-based materials, oxide semiconductors, carbon nanotubes, and graphene. A layered structure of layers each containing any of these elements may also be used. The material used to form the first or second electrode may also be an organic material (conductive polymer) such as poly(3,4-ethylenedioxythiophene)/polystyrene sulfonic acid [PEDOT/PSS]. Any of these conductive materials may be mixed with a binder (polymer) to form a paste or ink composition, which may be cured to form an electrode to be used. Examples of methods for forming the first or second electrode, which depend on the material used to form the electrodes, include various PVD techniques; various CVD techniques including MOCVD techniques; various coating methods; lift-off processes; sol-gel methods; electro-deposition techniques; shadow mask methods; plating such as electroplating, electroless plating, or a combination thereof; and spraying methods, any of which may be used in combination with patterning techniques if necessary. Examples of the substrate include organic polymers (including polymer materials in the form of a flexible plastic film, sheet, or substrate) such as poly(methyl methacrylate) (PMMA), polyvinyl alcohol (PVA), polyvinyl phenol (PVP), polyethersulfone (PES), polyimide, polycarbonate (PC), polyethylene terephthalate (PET), and polyethylene naphthalate (PEN), or mica. For example, the use of a substrate made of such a flexible polymer material enables the device to be incorporated or integrated into an electronic apparatus. Other examples of the substrate include various glass substrates, various glass substrates whose surface is coated with an insulating film, quartz substrates, quartz substrates whose surface is coated with an insulating film, silicon substrates whose surface is coated with an insulating film, and metal substrates made of various metals or alloys such as stainless steel. The insulating film may be made of a silicon oxide-based material (e.g., $SiO_x$ or spin-on-glass (SOG)); silicon nitride ($SiN_y$); silicon oxynitride (SiON); aluminum oxide ($Al_2O_3$); or a metal oxide or a metal salt. A conductive substrate (a substrate made of a metal such as gold or aluminum or a substrate made of highly oriented graphite) whose surface is coated with such an insulating film may also be used. The surface of the substrate is preferably smooth, but may have roughness to such an extent that the characteristics of the photoelectric conversion material layer are not adversely affected. The adhesion between the substrate and the first or second electrode may be improved by forming, on the surface of the substrate, a silanol derivative by a silane coupling method, a thin film of a thiol derivative, a carboxylic acid derivative, or a phosphoric acid derivative by an SAM method or the like, or a thin film of an insulating metal salt or metal complex by CVD or the like. The transparent substrate is intended to include a substrate made of a material that does not excessively absorb light to be incident on the photoelectric conversion material layer through the substrate.

In some cases, the electrode or the photoelectric conversion material layer may be covered with a coating layer. Examples of materials used to form the coating layer not only include inorganic insulating materials for high-dielectric metal oxide insulating films, such as silicon oxide-based materials; silicon nitride (SiNY); and aluminum oxide ($Al_2O_3$); but also include organic insulating materials (organic polymers) such as poly(methyl methacrylate) (PMMA); polyvinyl phenol (PVP); polyvinyl alcohol (PVA); polyimide; polycarbonate (PC); polyethylene terephthalate (PET); polystyrene; silanol derivatives (silane coupling agents) such as N-2-(aminoethyl)-3-aminopropyltrimethoxysilane (AEAPTMS), 3-mercaptopropyltrimethoxysilane (MPTMS), and octadecyltrichlorosilane (OTS); and straight-chain hydrocarbons having, at one end, a functional group capable of bonding to the electrode, such as octadecanethiol and dodecyl isocyanate. Any combination thereof may also be used. Examples of silicon oxide-based materials include silicon oxide ($SiO_x$), BPSG, PSG, BSG, AsSG, PbSG, silicon oxynitride (SiON), SOG (spin-on-glass), and low-dielectric materials (e.g., polyaryl ether, cycloperfluorocarbon polymers, and benzocyclobutene, cyclic fluororesin, polytetrafluoroethylene, fluorinated aryl ether, fluorinated polyimide, amorphous carbon, and organic SOG).

In the photoelectric transducer etc. of the present invention, the thickness of the photoelectric conversion material layer is typically, but not limited to, $2.5 \times 10^{-8}$ m to $3 \times 10^{-7}$ m, preferably $2.5 \times 10^{-8}$ m to $2 \times 10^{-7}$ m, more preferably $1 \times 10^{-7}$ m to $1.8 \times 10^{-7}$ m. The azo moiety-containing thiazole compound represented by the structural formula (1) or (2) has a high absorption coefficient ($\alpha$). Thus, the photoelectric conversion material layer can be made thinner, which makes it possible to solve the problem of disadvantages of conventional organic materials, such as high resistance, low mobility, and low carrier density, and to provide a photoelectric transducer or a solid-state imaging apparatus with high sensitivity and high response speed. As the photoelectric conversion material layer is made thinner, a higher electric field intensity E can be applied to the photoelectric conversion material layer under the application of the same potential, so that a higher photocurrent can be obtained even though the mobility or carrier density is relatively low. Methods for forming the photoelectric conversion material layer include application methods, PVD techniques; and various CVD techniques including MOCVD techniques. Examples of the application methods include spin coating methods; immersion methods; cast methods; various printing methods such as screen printing, inkjet printing, offset printing, and gravure printing; stamping methods; spraying methods; and various coating methods such as air doctor coater method, blade coater method, rod coater method, knife coater method, squeeze coater method, reverse roll coater method, transfer roll coater method, gravure coater method, kiss coater method, cast coater method, spray coater method, slit orifice coater method, and calender coater method. A nonpolar or low-polarity organic solvent such as toluene, chloroform, hexane, or ethanol may be used in the application methods. Examples of the PVD techniques include various vacuum deposition methods such as electron beam heating, resistive heating, and flash deposition; plasma deposition techniques; various sputtering techniques such as bipolar sputtering, direct current sputtering, direct current magnetron sputtering, high frequency sputtering, magnetron sputtering, ion beam sputtering, and bias sputtering; and various ion plating techniques such as DC (direct current) methods, RF methods, multi-cathode methods, activated reactive evaporation, field evaporation, high-frequency ion plating, and reactive ion plating. Alternatively, when photoelectric transducers are integrated to form a solid-state imaging apparatus, patterning methods based on PLD (pulsed laser deposition) may also be used.

The base on which the photoelectric conversion material layer is to be formed, specifically, the first electrode or the substrate, preferably has a surface roughness $R_a$ of 1.0 nm or less. When the base is planarized, the molecules used to form the photoelectric conversion material layer can be orderly arranged in each of the horizontal and vertical directions, so that the resulting structure is less likely to cause a significant voltage drop at the interface between the photoelectric conversion material layer and the first electrode. It is widely known that such a voltage drop is caused by lattice mismatch at the interface between the photoelectric conversion material layer and the first electrode and leads to defect-level formation or an increase in interface resistance, which results in the inhibition of carrier movement between the first electrode and the photoelectric conversion material layer. A planarizing layer may be formed between the photoelectric conversion material layer and the substrate. The planarizing layer may also have the function of preventing reflection of light having passed through the substrate. The planarizing layer may be made of poly(methyl methacrylate), polyvinyl alcohol, polyvinyl phenol, polyethersulfone, polyimide, polycarbonate, polyethylene terephthalate, polyethylene naphthalate, a silicon oxide-based material, silicon nitride, silicon oxynitride, or aluminum oxide.

The surface of the first electrode as the base on which the photoelectric conversion material layer is to be formed may be subjected to plasma ashing. At least one gas species selected from Ar, $N_2$, and $O_2$ may be used in the plasma ashing. When the surface of the first electrode is subjected to plasma ashing, variations in photoelectric conversion and the level of noise in photoelectric conversion have been reduced while the photocurrent value is kept constant, and the dark current level has been successfully reduced to 1 nanoampere/$cm^2$. Such a reduction in dark current level makes it possible to provide an organic photoelectric transducer having a wide dynamic range and capable of achieving high sensitivity for contrast.

In the structural formula (1) or (2), the substituent X or Y may be an alkyl group such as methyl, ethyl, propyl, isopropyl, tert-butyl, pentyl, hexyl, octyl, or dodecyl. There is no restriction as to whether the alkyl group is linear or branched. The substituent X or Y may be a cycloalkyl group such as cyclopentyl or cyclohexyl; an alkenyl group such as vinyl; an alkynyl group such as ethynyl; an aryl group such as phenyl, naphthyl, or biphenyl; an arylalkyl group such as methylaryl, ethylaryl, isopropylaryl, n-butylaryl, p-tolyl, p-ethylphenyl, p-isopropylphenyl, 4-propylphenyl, 4-butylphenyl, or 4-nonylphenyl; an aromatic heterocyclic ring such as pyridyl, thienyl, furyl, pyridazinyl, pyrimidinyl, pyrazinyl, triazinyl, imidazolyl, pyrazolyl, thiazolyl, quinazolinyl, or phthalazinyl; a heterocyclic ring group such as pyrrolidyl, imidazolidyl, morpholyl, or oxazolidyl; an alkoxy group such as methoxy, ethoxy, propyloxy, pentyloxy, or hexyloxy; a cycloalkoxy group such as cyclopentyloxy or cyclohexyloxy; an aryloxy group such as phenoxy or naphthyloxy; an alkylthio group such as methylthio, ethylthio, propylthio, pentylthio, or hexylthio; a cycloalkylthio group such as cyclopentylthio or cyclohexylthio; an arylthio group such as phenylthio or naphthylthio; an alkoxycarbonyl group such as methyloxycarbonyl, ethyloxycarbonyl, butyloxycarbonyl, or octyloxycarbonyl; an aryloxycarbonyl group such as phenyloxycarbonyl or naphthyloxycarbonyl; a sulfamoyl group such as aminosulfonyl, methylaminosulfonyl, dimethylaminosulfonyl, cyclohexylaminosulfonyl, phenylaminosulfonyl, naphthylaminosulfonyl, or 2-pyridylaminosulfonyl; an acyl group such as acetyl, ethylcarbonyl, propylcarbonyl, cyclohexylcarbonyl, octylcarbonyl, 2-ethylhexylcarbonyl, dodecylcarbonyl, phenylcarbonyl, naphthylcarbonyl, or pyridylcarbonyl; a thiocarbonyl group such as thioacetyl, ethylthiocarbonyl, propylthiocarbonyl, cyclohexylthiocarbonyl, octylthiocarbonyl, 2-ethylhexylthiocarbonyl, dodecylthiocarbonyl, phenylthiocarbonyl, naphthylthiocarbonyl, or pyridylthiocarbonyl; an acyloxy group such as acetyloxy, ethylcarbonyloxy, octylcarbonyloxy, or phenylcarbonyloxy; an amide group such as methylcarbonylamino, ethylcarbonylamino, dimethylcarbonylamino, pentylcarbonylamino, cyclohexylcarbonylamino, 2-ethylhexylcarbonylamino, phenylcarbonylamino, or naphthylcarbonylamino; a carbamoyl group such as aminocarbonyl, methylaminocarbonyl, dimethylaminocarbonyl, cyclohexylaminocarbonyl, 2-ethylhexylaminocarbonyl, phenylaminocarbonyl, naphthylaminocarbonyl, or 2-pyridylaminocarbonyl; a ureido group such as methylureido, ethylureido, cyclohexylureido, dodecylureido, phenylureido, naphthylureido, or 2-pyridylaminoureido; a sulfinyl group such as methylsulfinyl, ethylsulfinyl, butylsulfinyl, cyclohexylsulfinyl, 2-ethylhexylsulfinyl, phenylsulfinyl, naphthylsulfinyl, or 2-pyridylsulfinyl; an alkylsulfonyl group such as methylsulfonyl, ethylsulfonyl, butylsulfonyl, cyclohexylsulfonyl, 2-ethylhexylsulfonyl, or dodecylsulfonyl; an arylsulfonyl group such as phenylsulfonyl, naphthylsulfonyl, or 2-pyridylsulfonyl; an amino group such as amino, ethylamino, dimethylamino, butylamino, 2-ethylhexylamino, anilino, naphthylamino, or 2-pyridylamino; a halogen atom such as a fluorine atom, a chlorine atom, a bromine atom, or an iodine atom; or a fluorohydrocarbon group such as fluoromethyl, trifluoromethyl, pentafluoroethyl, or pentafluorophenyl. The substituent X or Y may also be a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, or a silyl group such as trimethylsilyl, triisopropylsilyl, triphenylsilyl, or phenyldiethylsilyl. The substituents listed above may also be substituted with any of the above substituents. Two or more of these substituents may be coupled together to form a ring.

The substituent $R_1$ in the structural formula (1) or the substituents $R_2$ to $R_6$ in the structural formula (2) may each be an alkyl group such as methyl, ethyl, propyl, isopropyl, tert-butyl, pentyl, hexyl, octyl, or dodecyl. There is no restriction as to whether the alkyl group is linear or branched. The substituents $R_1$ to $R_6$ may each be a cycloalkyl group such as cyclopentyl or cyclohexyl; an alkenyl group such as vinyl; an alkynyl group such as ethynyl; an aryl group such as phenyl, naphthyl, or biphenyl; an arylalkyl group such as methylaryl, ethylaryl, isopropylaryl, n-butylaryl, p-tolyl, p-ethylphenyl, p-isopropylphenyl, 4-propylphenyl, 4-butylphenyl, or 4-nonylphenyl; an aromatic heterocyclic ring such as pyridyl, thienyl, furyl, pyridazinyl, pyrimidinyl, pyrazinyl, triazinyl, imidazolyl, pyrazolyl, thiazolyl, quinazolinyl, or phthalazinyl; a heterocyclic ring group such as pyrrolidyl, imidazolidyl, morpholyl, or oxazolidyl; an alkoxy group such as methoxy, ethoxy, propyloxy, pentyloxy, or hexyloxy; a cycloalkoxy group such as cyclopentyloxy or cyclohexyloxy; an aryloxy group such as phenoxy or naphthyloxy; an alkylthio group such as methylthio, ethylthio, propylthio, pentylthio, or hexylthio; a cycloalkylthio group such as cyclopentylthio or cyclohexylthio; an arylthio group such as phenylthio or naphthylthio; an alkoxycarbonyl group such as methyloxycarbonyl, ethyloxycarbonyl, butyloxycarbonyl, or octyloxycarbonyl; an aryloxycarbonyl group such as phenyloxycarbonyl or naphthyloxycarbonyl; a sulfamoyl group such as aminosulfonyl, methylaminosulfonyl, dimethylaminosulfonyl, cyclohexylaminosulfonyl, phenylaminosulfonyl, naphthylaminosulfonyl, or 2-pyridylaminosulfonyl; an acyl group such as acetyl, ethylcarbonyl, propylcarbonyl, cyclohexylcarbonyl, octylcarbonyl, 2-ethylhexylcarbonyl, dodecylcarbonyl, phenylcarbonyl, naphthylcarbonyl, or pyridylcarbonyl; a thiocarbonyl group such as thioacetyl, ethylthiocarbonyl, propylthiocarbonyl, cyclohexylthiocarbonyl, octylthiocarbonyl, 2-ethylhexylthiocarbonyl, dodecylthiocarbonyl, phenylthiocarbonyl, naphthylthiocarbonyl, or pyridylthiocarbonyl; an acyloxy group such as acetyloxy, ethylcarbonyloxy, octylcarbonyloxy, or phenylcarbonyloxy; an amide group such as methylcarbonylamino, ethylcarbonylamino, dimethylcarbonylamino, pentylcarbonylamino, cyclohexylcarbonylamino, 2-ethylhexylcarbonylamino, phenylcarbonylamino, or naphthylcarbonylamino; a carbamoyl group such as aminocarbonyl, methylaminocarbonyl, dimethylaminocarbonyl, cyclohexylaminocarbonyl, 2-ethylhexylaminocarbonyl, phenylaminocarbonyl, naphthylaminocarbonyl, or 2-pyridylaminocarbonyl; a ureide group such as methylureido, ethylureido, cyclohexylureido, dodecylureido, phenylureido, naphthylureido, or 2-pyridylaminoureido; a sulfinyl group such as methylsulfinyl, ethylsulfinyl, butylsulfinyl, cyclohexylsulfinyl, 2-ethylhexylsulfinyl, phenylsulfinyl, naphthylsulfinyl, or 2-pyridylsulfinyl; an alkylsulfonyl group such as methylsulfonyl, ethylsulfonyl, butylsulfonyl, cyclohexylsulfonyl, 2-ethylhexylsulfonyl, or dodecylsulfonyl; an arylsulfonyl group such as phenylsulfonyl, naphthylsulfonyl, or 2-pyridylsulfonyl; an amino group such as amino, ethylamino, dimethylamino, butylamino, 2-ethylhexylamino, anilino, naphthylamino, or 2-pyridylamino; a halogen atom such as a fluorine atom, a chlorine atom, a bromine atom, or an iodine atom; or a fluorohydrocarbon group such as fluoromethyl, trifluoromethyl, pentafluoroethyl, or pentafluorophenyl. The substituents $R_1$ to $R_6$ may also each be a sulfo group, a cyano group, an isocyano group, a nitroso group, a nitro group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, or a silyl group such as trimethylsilyl, triisopropylsilyl, triphenylsilyl, or phenyldiethylsilyl. The substituents listed above may also be substituted with any of the above substituents. Two or more of these substituents may be coupled together to form a ring.

The solid-state imaging apparatus of the present invention may be of a front-side illumination type or a backside illumination type, or may form a single-chip, solid-state color imaging apparatus. The solid-state imaging device as a component of the solid-state imaging apparatus of the invention may further include on-chip microlenses and a light-shielding layer as needed. The solid-state imaging device may include photoelectric transducers (solid-state imaging elements), a drive circuit for driving the photoelectric transducers, and wiring. If necessary, the solid-state imaging device may include a shutter for controlling the incidence of light on the photoelectric transducers (solid-state imaging elements). The solid-state imaging device may also include optical cut filters depending on the purpose of the solid-state imaging apparatus. In the solid-state imaging apparatus of the invention, the solid-state imaging device may have a single layer of photoelectric transducers according to the invention. In this case, for example, examples of the arrangement of the photoelectric transducers include Bayer arrangement, inter-line arrangement, G stripe/RB checker arrangement, G stripe/RB full-checker arrangement, complementary color checker arrangement, stripe arrangement, oblique stripe arrangement, primary color difference arrangement, field color difference sequential arrangement, frame color difference sequential arrangement, MOS arrangement, modified MOS arrangement, frame interleave arrangement, and field interleave arrangement. The photoelectric transducer of the invention may be used as a component of not only an imaging apparatus (solid-state imaging apparatus) such as a television camera but also an optical sensor, an image sensor, or a solar cell.

EXAMPLE 1

Example 1 relates to the photoelectric transducers and the solid-state imaging apparatuses according to the first and second embodiments of the present invention. As shown in FIG. 1 (a schematic partial cross-sectional view), the photoelectric transducer 11 of Example 1 includes (a-1) first and second electrodes 21 and 22 separated from each other, and (a-2) a photoelectric conversion material layer 30 provided between the first and second electrodes 21 and 22. More specifically, the first electrode 21 is formed of a transparent conductive material on a transparent substrate 20, the photoelectric conversion material layer 30 is formed on the first electrode 21, and the second electrode 22 is formed on the photoelectric conversion material layer 30.

Specifically, the first electrode 21, which is a light-incident-side electrode, is made of a transparent conductive material, more specifically 120-nm-thick indium-tin oxide (ITO). The second electrode 22 is made of 100-nm-thick aluminum (Al). The first electrode 21 of the transparent conductive material is formed on the transparent substrate 20. The photoelectric conversion material layer 30 is formed on the first electrode 21. The second electrode 22 is formed on the photoelectric conversion material layer 30. Light enters the photoelectric conversion material layer 30 through the substrate 20 and the first electrode 21. The substrate 20 is made of a 0.7-mm-thick quartz substrate. The first electrode 21 has a surface roughness $R_a$ of 0.28 nm and a surface roughness $R_{max}$ of 3.3 nm on the photoelectric conversion material layer side. In general, the first electrode 21 preferably has a surface roughness $R_a$ of 1.0 nm or less, more preferably 0.3 nm or less.

The photoelectric conversion material layer 30 is made of an azo moiety-containing thiazole compound represented by the structural formula (1) (the first embodiment of the present invention) or the structural formula (2) (the second embodiment of the invention). In Example 1, more specifically, the photoelectric conversion material layer 30 is made of 4-(2-thiazolylazo)resorcinol represented by the structural formula (3) below, and absorbs blue light. The absorption coefficient of 4-(2-thiazolylazo)resorcinol is $3.45 \times 10^4$ $dm^3 mol^{-1} cm^{-1}$.

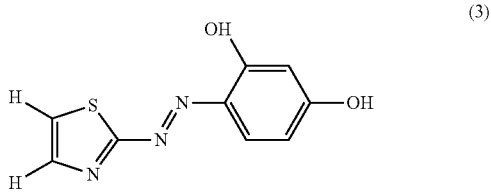 [SMILES: Oc1ccc(/N=N/c2nccs2)c(O)c1]

(3)

The photoelectric transducer 11 of Example 1 was produced by the method described below. First, the first electrode 21 of 100-nm-thick ITO is formed on the substrate 20 based on a photolithographic technique using a photomask. Subsequently, a bump 31 of an insulating material is formed on the substrate 20 and the first electrode 21, and then the photoelectric conversion material layer 30 (107 nm in thickness) of the azo moiety-containing thiazole compound represented by the structural formula (1), (2), or (3) is formed (deposited) on the first electrode 21 and the bump 31 by vacuum deposition using a metal mask. The temperature of the substrate is set at room temperature (25° C.) during the vacuum deposition, and the photoelectric conversion material layer 30 is formed at a deposition rate of 0.1 nm/second. Subsequently, the second electrode 22 of 100-nm-thick aluminum is formed on the photoelectric conversion material layer 30 and the substrate 20 by PVD using a metal mask. The second electrode 22 is formed under the following conditions. The temperature of the substrate is set at room temperature (25° C.), and the second electrode 22 is formed at a deposition rate of 0.5 nm/second. The bump 31 is formed to surround the region of the substrate 20 on which the photoelectric conversion material layer 30 is to be formed. Before the photoelectric conversion material layer 30 is formed, the first electrode 21 and the bump 31, which are used as the base, are subjected to an UV ozone treatment. In Examples 2 and 3 described below, the photoelectric transducer is successfully produced by the same method.

Figure 2:
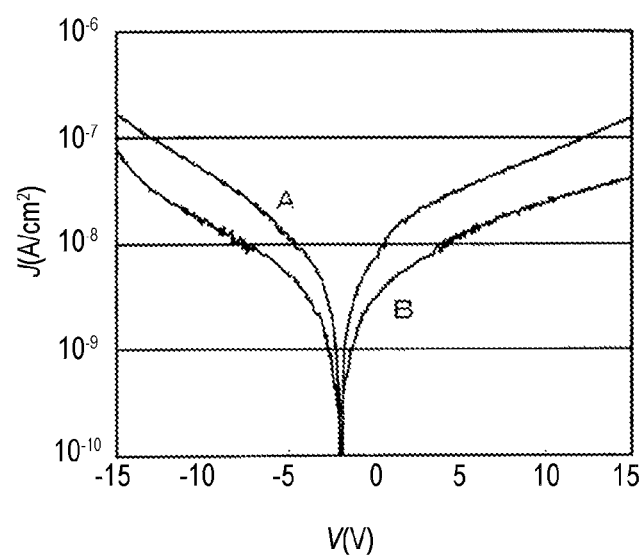
FIG. 2 is a graph showing the current-voltage curves of the photoelectric transducer of Example 1, which are obtained when light with a wavelength of 480 nm is applied thereto and when no light is applied thereto, respectively.

FIG. 2 shows the current-voltage curves of the resulting photoelectric transducer 11 of Example 1, in which the curve A is obtained when light with a wavelength of 480 nm is applied to it, and the curve B is obtained when light is not applied. In FIG. 2, the vertical axis represents the value of the current flowing therethrough, and the horizontal axis represents the voltage applied to the second electrode. The first electrode is grounded. FIG. 2 shows that the current flowing through the photoelectric transducer 11 changes depending on whether or not light with a wavelength of 480 nm is applied, and photocurrent on-off response is produced when light with a wavelength of 480 nm is applied.

Figure 3:
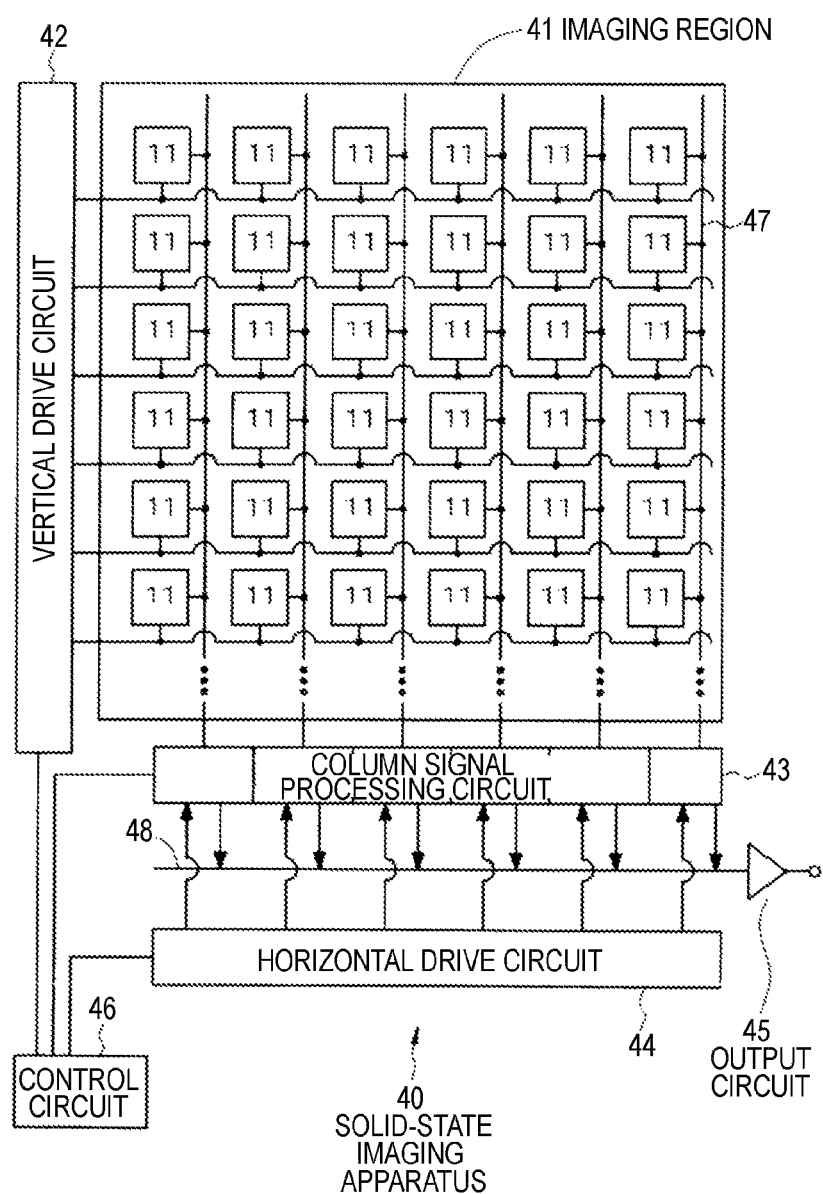
FIG. 3 is a schematic diagram of a solid-state imaging apparatus of Example 1.

FIG. 3 is a schematic diagram showing the solid-state imaging apparatus (solid-state imaging device) of Example 1. In Examples 2 and 3 described below, the solid-state imaging apparatus (solid-state imaging device) has the same features and structure as the solid-state imaging apparatus (solid-state imaging device) of Example 1. The solid-state imaging apparatus 40 of Example 1 includes an imaging region 41 having the photoelectric transducers 11 arranged in a two-dimensional array on a semiconductor substrate (e.g., Si substrate), and peripheral circuits therefor, such as a vertical drive circuit 42, a column signal processing circuit 43, a horizontal drive circuit 44, an output circuit 45, and a control circuit 46. It will be understood that these circuits may include well-known circuits and that other circuit structures (e.g., various circuits used in conventional CCD or CMOS imaging apparatuses) may also be used to form the apparatus.

The control circuit 46 produces clock or control signals for the operation of the vertical drive circuit 42, the column signal processing circuit 43, and the horizontal drive circuit 44 based on vertical synchronizing signals, horizontal synchronizing signals, and master clock. The produced clock or control signals are input to the vertical drive circuit 42, the column signal processing circuit 43, and the horizontal drive circuit 44.

The vertical drive circuit 42, for example, which includes shift registers, sequentially selects and scans each row of the photoelectric transducers 11 in the vertical direction in the imaging region 41. The pixel signal based on the current (signal) produced depending on the quantity of light incident on each photoelectric transducer 11 is sent to the column signal processing circuit 43 through a vertical signal line 47.

The column signal processing circuit 43, for example, which is arranged for each column of the photoelectric transducers 11, processes the signal output from a row of the photoelectric transducers 11 for noise reduction or signal amplification for each photoelectric transducer by using the signal from black reference pixels (which are formed around the effective pixel region although not shown). Horizontal selection switches (not shown) are provided at the output stage of the column signal processing circuit 43 and connected between a horizontal signal line 48 and the column signal processing circuit 43.

The horizontal drive circuit 44, for example, which includes shift registers, sequentially selects each column signal processing circuit 43 by sequentially outputting horizontal scanning pulses, and outputs a signal from each column signal processing circuit 43 to the horizontal signal line 48.

The output circuit 45 processes signals sequentially supplied from each column signal processing circuit 43 through the horizontal signal line 48, and outputs the processed signals.

EXAMPLE 2

Figure 4:
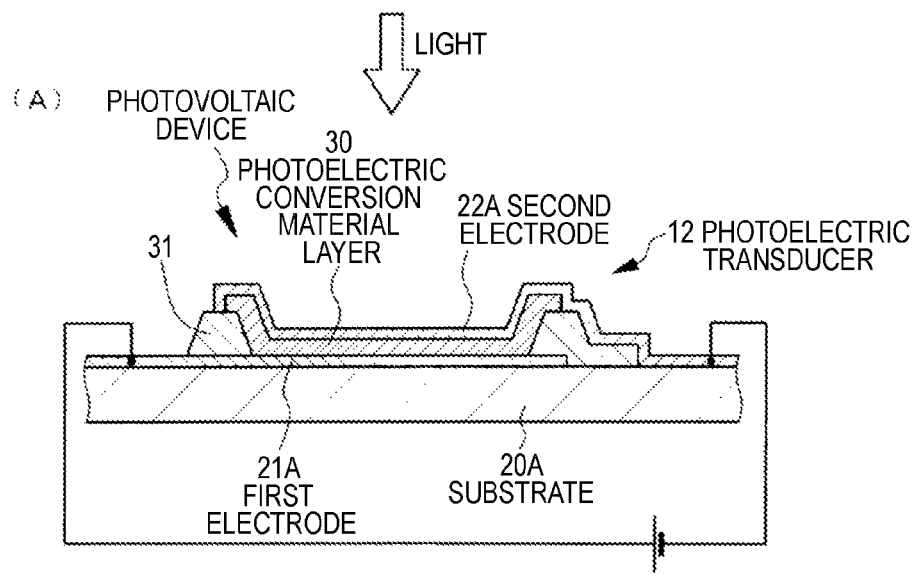
FIGS. 4(A) and 4(B) are schematic cross-sectional views of photoelectric transducers of Examples 2 and 3.
Figure 4:
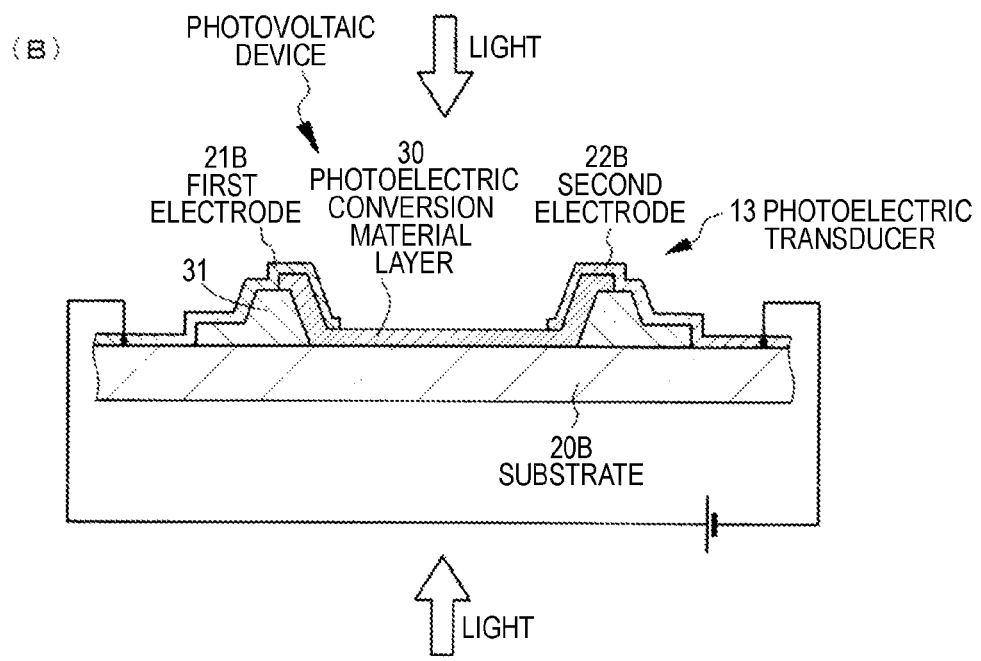

Example 2 provides a modification of the photoelectric transducer of Example 1. As shown in FIG. 4(A) (a schematic partial cross-sectional view), the photoelectric transducer 12 of Example 2 includes a first electrode 21A formed on a substrate 20A, a photoelectric conversion material layer 30 formed on the first electrode 21A, and a second electrode 22A formed of a transparent conductive material on the photoelectric conversion material layer 30. Light enters the photoelectric conversion material layer 30 through the second electrode 22A. Specifically, for example, the substrate 20A is made of a silicon semiconductor substrate, the first electrode 21A is made of aluminum, and the second electrode 22A is made of ITO. Except for this point, the features and structure of the photoelectric transducer 12 of Example 2 may be the same as those of the photoelectric transducer 11 of Example 1, and thus a detailed description thereof is omitted.

EXAMPLE 3

Example 3 provides a modification of the photoelectric transducer of Example 1. As shown in FIG. 4(B) (a schematic partial cross-sectional view), the photoelectric transducer 13 of Example 3 includes first and second electrodes 21B and 22B formed on a substrate, and a photoelectric conversion material layer 30 formed to reach the first and second electrodes 21B and 22B and formed on the substrate 20B. Light enters the photoelectric conversion material layer 30 through the second electrode 22B. Alternatively, light enters the photoelectric conversion material layer 30 through the substrate 20B and the first electrode 21B. Specifically, for example, the substrate 20B is made of a silicon semiconductor substrate, and the first and second electrodes 21B and 22B are each made of a metal material or a transparent conductive material. Except for this point, the features and structure of the photoelectric transducer 13 of Example 3 may be the same as those of the photoelectric transducer 11 of Example 1, and thus a detailed description thereof is omitted.

While the present invention has been described with reference to preferred examples, the preferred examples are not intended to limit the present invention. The structure and features of the photoelectric transducers and the solid-state imaging apparatuses, the production conditions, the production methods, and the materials used, described in the examples are only illustrative and may be changed as needed. The photoelectric conversion material layer may include a single thiazole compound having an azo moiety or a mixture of two or more thiazole compounds each having an azo moiety. Alternatively, two or more photoelectric conversion material layers may be stacked, in which the respective photoelectric conversion material layers may include different azo moiety-containing thiazole compounds. For example, the photoelectric transducer described in Example 1 may be provided on a silicon semiconductor substrate, and one or more layers (e.g., two layers) of photoelectric conversion region may be provided inside the silicon semiconductor substrate, which is located below the photoelectric transducer, so that a layered structure of photoelectric transducers (light-receiving regions), specifically, a solid-state imaging apparatus having a structure with layered subpixels, can be provided. In such a solid-state imaging apparatus, for example, the photoelectric transducer described in Example 1 can receive blue light, and one or more layers of photoelectric conversion region provided inside the silicon semiconductor substrate can receive light of other colors. Instead of providing photoelectric conversion regions inside the silicon semiconductor substrate, photoelectric conversion regions may be formed on the semiconductor substrate by epitaxial growth, or formed on a silicon layer with what is called SOI structure. The photoelectric transducer of the present invention may also be provided to function as a solar cell. In this case, light may be applied to the photoelectric conversion material layer with no voltage applied between the first and second electrodes.

REFERENCE SIGNS LIST

11 PHOTOELECTRIC TRANSDUCER
20 SUBSTRATE
21 FIRST ELECTRODE
22 SECOND ELECTRODE
30 PHOTOELECTRIC CONVERSION MATERIAL LAYER
31 BUMP
40 SOLID-STATE IMAGING APPARATUS
41 IMAGING REGION
42 VERTICAL DRIVE CIRCUIT
43 COLUMN SIGNAL PROCESSING CIRCUIT
44 HORIZONTAL DRIVE CIRCUIT
45 OUTPUT CIRCUIT
46 CONTROL CIRCUIT
47 VERTICAL SIGNAL LINE
48 HORIZONTAL SIGNAL LINE

The invention claimed is:
1. A solid-state imaging apparatus comprising:
a plurality of photoelectric transducers, each photoelectric transducer comprising:
(a-1) first and second electrodes separated from each other;
(a-2) a first photoelectric conversion material layer provided between the first and second electrodes, wherein the first photoelectric conversion material layer comprises a first azo moiety-containing thiazole compound represented by the following structural formula (1):

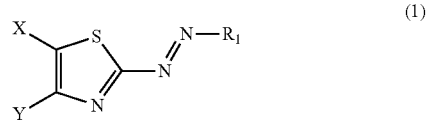

where X and Y each represent a hydrogen atom or a substituent other than a hydrogen atom, and $R_1$ represents an alkyl group, an alkenyl group, an alkynyl group, or an aryl group; and
(a-3) at least one electrical circuit in electrical communication with each photoelectric transducer.
2. The solid-state imaging apparatus according to claim 1, wherein
X and Y each represent a substituent other than a hydrogen atom, and the substituent is selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, and a silyl group.

3. The solid-state imaging apparatus according to claim 1, wherein
the electrode on a light incident side comprises a transparent conductive material.

4. The solid-state imaging apparatus according to claim 2, wherein
the electrode on a light incident side comprises a transparent conductive material.

5. The solid-state imaging apparatus according to claim 1, wherein at least one of the plurality of photoelectric transducers further comprises a second photoelectric conversion material layer.

6. The solid-state imaging apparatus according to claim 5, wherein the second photoelectric conversion material layer comprises a second azo moiety-containing thiazole compound, wherein the second azo moiety-containing thiazole compound is different from the first azo moiety-containing thiazole compound.

7. The solid-state imaging apparatus according to claim 5, wherein the first photoelectric conversion material layer absorbs light having a wavelength in a first range and the second photoelectric conversion material layer absorbs light having a wavelength in a second range, wherein at least a portion of the second range does not fall within the first range.

8. The solid-state imaging apparatus according to claim 1, wherein the apparatus further comprises a substrate, wherein each of the plurality of photoelectric transducers is positioned on the substrate.

9. A solid-state imaging apparatus comprising:
a plurality of photoelectric transducers, each photoelectric transducer comprising:
(a-1) first and second electrodes separated from each other;
(a-2) a first photoelectric conversion material layer provided between the first and second electrodes, wherein the first photoelectric conversion material layer comprises a first azo moiety-containing thiazole compound represented by the following structural formula (2):

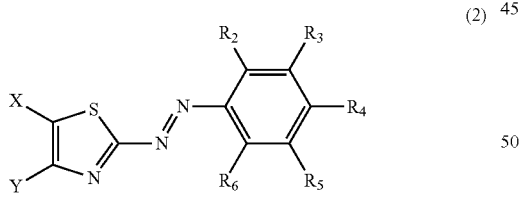

(2)

where X and Y each represent a hydrogen atom or a substituent other than a hydrogen atom, and at least one of $R_2$ to $R_6$ represents a substituent other than a hydrogen atom; and
(a-3) at least one electrical circuit in electrical communication with each photoelectric transducer.

10. The solid-state imaging apparatus according to claim 9, wherein
at least one of $R_2$ to $R_6$ represents an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, and a silyl group.

11. The solid-state imaging apparatus according to claim 9, wherein
X and Y each represent a substituent other than a hydrogen atom, and the substituent is selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, and a silyl group.

12. The solid-state imaging apparatus according to claim 10, wherein
X and Y each represent a substituent other than a hydrogen atom, and the substituent is selected from the group consisting of an alkyl group, a cycloalkyl group, an alkenyl group, an alkynyl group, an aryl group, an arylalkyl group, an aromatic heterocyclic ring, a heterocyclic group, an alkoxy group, a cycloalkoxy group, an aryloxy group, an alkylthio group, a cycloalkylthio group, an arylthio group, an alkoxycarbonyl group, an aryloxycarbonyl group, a sulfamoyl group, an acyl group, a thiocarbonyl group, an acyloxy group, an amide group, a carbamoyl group, a ureide group, a sulfinyl group, an alkylsulfonyl group, an arylsulfonyl group, an amino group, a halogen atom, a fluorohydrocarbon group, a cyano group, an isocyano group, a nitro group, a nitroso group, a carboxylic acid cyanide group, a cyanate group, an isocyanate group, a thiocyanate group, an isothiocyanate group, a formyl group, a thioformyl group, a hydrazide group, a hydroxy group, a sulfanyl group, a sulfo group, and a silyl group.

13. The solid-state imaging apparatus according to claim 9, wherein
the electrode on a light incident side comprises a transparent conductive material.

14. The solid-state imaging apparatus according to claim 10, wherein
the electrode on a light incident side comprises a transparent conductive material.

15. The solid-state imaging apparatus according to claim 11, wherein
the electrode on a light incident side comprises a transparent conductive material.

16. The solid-state imaging apparatus according to claim 9, wherein each of the plurality of photoelectric transducers further comprises a second photoelectric conversion material layer.

17. The solid-state imaging apparatus according to claim 16, wherein for each photoelectric transducer, the second photoelectric conversion material layer comprises a second azo moiety-containing thiazole compound, wherein the second azo moiety-containing thiazole compound is different from the first azo moiety-containing thiazole compound.

18. The solid-state imaging apparatus according to claim 16, wherein for each photoelectric transducer, the first photoelectric conversion material layer absorbs light having a wavelength in a first range and the second photoelectric conversion material layer absorbs light having a wavelength in a second range, wherein at least a portion of the second range does not fall within the first range.

19. The solid-state imaging apparatus according to claim 9, wherein the apparatus further comprises a substrate, wherein each of the plurality of photoelectric transducers is positioned on the substrate.

\* \* \* \* \*